United States Patent
Deinlein-Kalb et al.

(10) Patent No.: US 6,449,513 B1
(45) Date of Patent: Sep. 10, 2002

(54) METHOD FOR INHIBITING PAIN IMPULSES IN THE NERVE PATHWAYS OF HUMAN BEINGS AND ANIMALS

(75) Inventors: Hans Deinlein-Kalb; Marianne Deinlein-Kalb, both of Nuremberg (DE)

(73) Assignee: Monika Festl, Nuremberg (DE)

( * ) Notice: Subject to any disclaimer, the term of this patent is extended or adjusted under 35 U.S.C. 154(b) by 0 days.

(21) Appl. No.: 09/381,837
(22) PCT Filed: Feb. 10, 1998
(86) PCT No.: PCT/EP98/00732
§ 371 (c)(1),
(2), (4) Date: Sep. 24, 1999
(87) PCT Pub. No.: WO98/42404
PCT Pub. Date: Oct. 1, 1998

(30) Foreign Application Priority Data

Mar. 25, 1997 (DE) .......................................... 197 12 455

(51) Int. Cl.[7] .................................................. A61N 1/14
(52) U.S. Cl. .............................. 607/46; 607/2; 128/898
(58) Field of Search .................................. 607/115, 144, 607/145, 149, 150, 151, 152, 81, 75, 2, 1, 46; 361/212; 128/898

(56) References Cited

U.S. PATENT DOCUMENTS

| | | | | |
|---|---|---|---|---|
| 1,021,787 A | * | 4/1912 | McMurtry | .................. 472/75 |
| 1,090,682 A | * | 3/1914 | Brown | .................. 607/144 |
| 3,596,134 A | * | 7/1971 | Burke | .................. 361/220 |
| 4,654,746 A | * | 3/1987 | Lewis, Jr. et al. | .......... 361/212 |
| 4,703,754 A | * | 11/1987 | Ibbott | .................. 607/144 |
| 5,179,497 A | * | 1/1993 | Bakhoum | .................. 361/212 |
| 5,247,420 A | * | 9/1993 | Bakhoum | .................. 361/212 |
| 5,607,453 A | | 3/1997 | Ishiguro et al. | |
| 5,782,875 A | * | 7/1998 | Ledbetter | .................. 607/2 |
| 5,906,638 A | * | 5/1999 | Shimoda | .................. 607/152 |
| 6,014,585 A | * | 1/2000 | Stoddard | .................. 128/898 |

FOREIGN PATENT DOCUMENTS

| | | |
|---|---|---|
| DE | 1 701 259 | 4/1955 |
| DE | 35 00 379 | 7/1986 |
| EP | 296 248 | 12/1988 |
| GB | 2 025 237 | 1/1980 |
| WO | WO 92/10113 | 6/1992 |

* cited by examiner

Primary Examiner—Kennedy Schaetzle
(74) Attorney, Agent, or Firm—Sughrue Mion, PLLC

(57) ABSTRACT

According to a method of inhibiting pain pulses in the nerves of humans and animals and a device for carrying out the method the positive pole of an electrically uncharged capacitor is contacted with the skin surface around the place of pain in the body or the excited nerve from outside or fixedly applied there. In an excitation state, caused by a state of pain, of the nerves the pulse-like voltage peaks, which arise on voltage reversal in the nerves, are reduced or completely smoothed out by the electric flux of the capacitor.

16 Claims, 4 Drawing Sheets

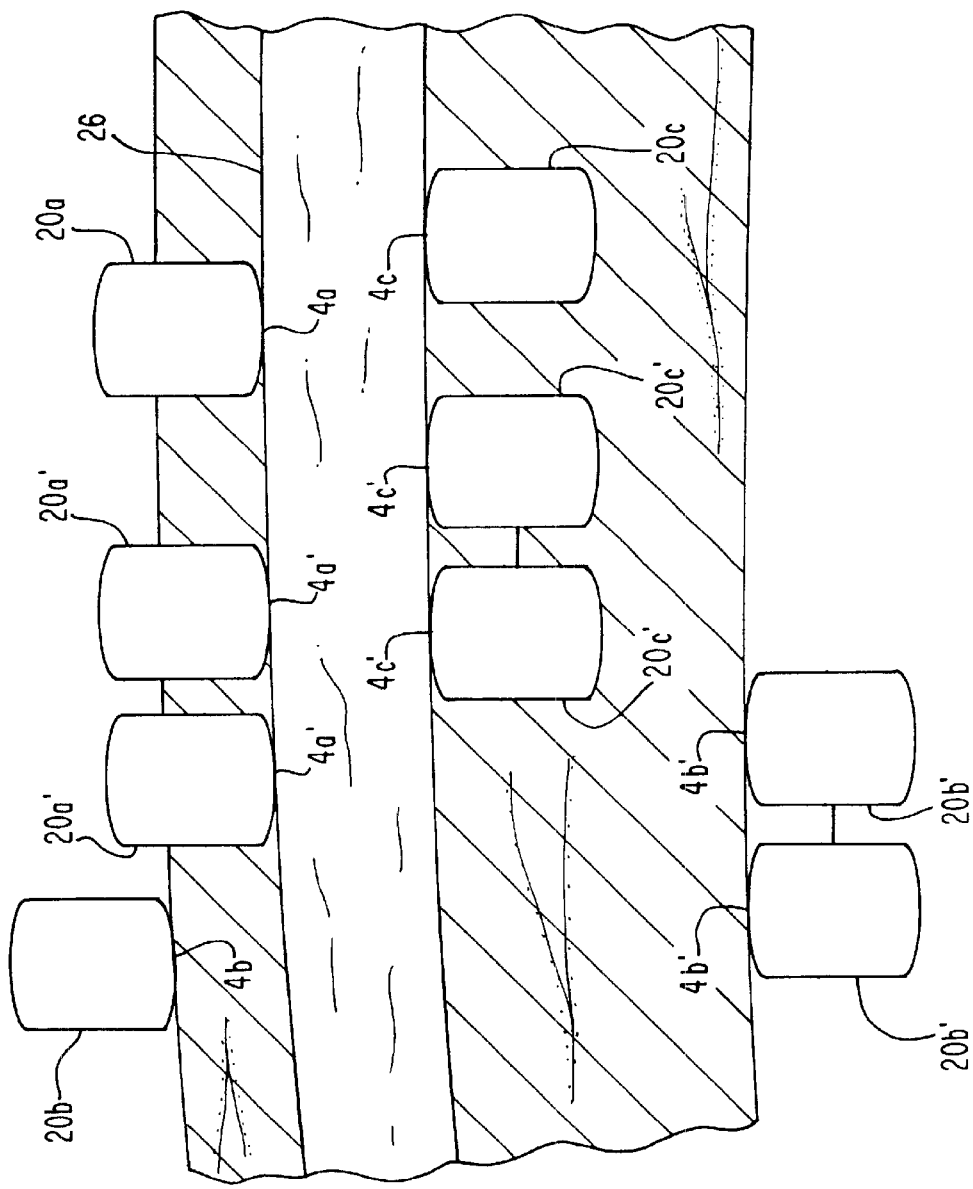

METHOD FOR INHIBITING PAIN IMPULSES IN THE NERVE PATHWAYS OF HUMAN BEINGS AND ANIMALS

DESCRIPTION

The invention relates to a method and device for inhibiting pain pulses in the nerves of humans and animals.

Pain is one of the commonest symptoms of illness or tissue damage or a metabolic disturbance. The pain is noticeable when mechanical, thermal, chemical or electrical stimuli exceed a certain threshold value.

Therapeutic analgesics which to some extent have a very strong action with just as strong side effects for humans, animals and the environment are used in combating pain.

Pain conduction in the nerve paths of humans and animals takes place by ions which migrate along to the electrically charged membrane of the nerve. A quiescent membrane is positively charged outside and negatively charged inside. The potential or voltage of the outer side relative to the inside is about 70 millivolts (mV) in the pain-free quiescent state (equilibrium rest potential). At the moment of excitation by pain, the changes reverse, whereby In the case of humans the potential decays over $\frac{1}{1000}$ second by about 100 mV to the negative side, i.e. to a value of −30 mV from the outside to the inside. The frequency of the rising and falling phase, which occurs due to migration of ions, of the peak potential is approximately proportional to the intensity of pain to be transmitted. The speed of conduction of the nerve action can be up to 100 m/sec in the case of humans.

The invention therefore has the object of providing a method and a device for the inhibiting of pain pulses in the nerves of humans and animals, which do not have the disadvantages of medicinal treatment of pain, are completely free of side effects, function without auxiliary energy, can be made and sold economically and do not cause any environmental loading in operation and disposal of waste.

This object is met by the features indicated in claim 1.

In further refinement of the invention it is regarded as advantageous that:

a) the capacitor or several capacitors in parallel connection are accommodated in a dosed housing, that the positive pole of the or each capacitor is connected with a large-area spherically rounded metal shell and the negative pole of the or each capacitor similarly with an oppositely disposed, spherically rounded metal shell, and that the negative potential is led to ground by way of the hand of the patient or the therapist;

b) the capacitance of the capacitor or the total capacitance of the capacitors connected in parallel is at least 10,000 microfarads ($\mu F$);

c) one or more capacitors are mounted in fixed location in furniture for sifting or lying on or in the bed of the patient and that the positive pole or poles thereof comes or come to constantly bear against the places of pain in the patient and the negative pole or poles is or are applied to ground and d) one or more capacitors in special flat mode of construction are held by means of a bandage at the pain-conducting parts of the body or held in the clothing of the patient against the pain-conducting parts of the body, wherein the positive pole is directed to the place of pain and the negative pole is drained off to a remote part of the body.

BRIEF DESCRIPTION OF THE DRAWINGS

The subject of the invention is described in the following.

An embodiment of the subject of the invention for manual use is reproduced in FIG. 1; and various implementations of the present invention are shown in FIGS. 2–5.

Figure 1:
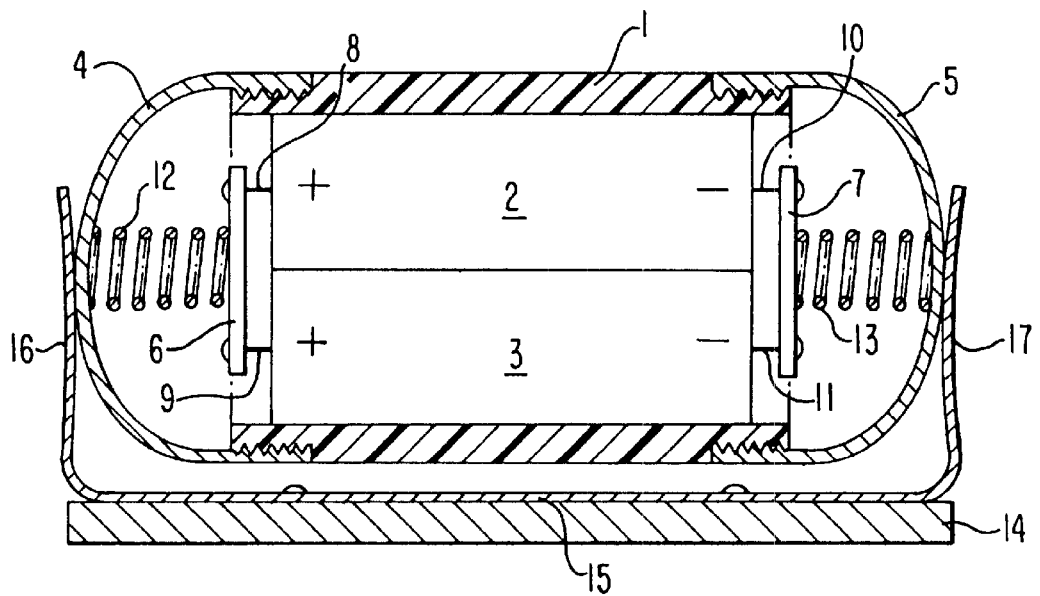

The subject of the invention consists of a tubular housing 1, electric capacitors 2 and 3, metal shells 4 and 5, contact plates 6 and 7, conductor wires 8, 9. 10 and 11, compression springs 12 and 13, and spring holder 14 with spring clips 16 and 17 and connecting web 15.

Installed In the tubular housing 1, which consists of a nonconductive material, are, for example, two rod capacitors 2 and 3 which are parallel to the centre axis of the tubular housing 1 and from the cylindrical ends of which project the conductor wires 8, 9, 10 and 11. The respective like-poled ends of the conductor wires 8, 9 and 10, 11 are soldered to contact plates 6 and 7, so that a parallel connection of the capacitors 2 and 3 results. Screwed into the respective tube openings of the tubular housing 1 at both ends are metal shells 4 and 5, which produce a constant contact between the metal shells 4 and 5 and the capacitors 2 and 3 by way of the compression springs 12 and 13, the contact plates 6 and 7 and the conductor wires 8, 9, 10 and 11. The number of capacitors depends on the constructional design of the subject of the invention and on the size of the desired capacitor capacitance.

In readiness selling. i.e. when the subject of the invention is not in use, this is retained in a spring holder 14 in such a manner that the subject of the invention is clamped between two conductive spring clips 16 and 17, whereby a through-flow connection between the metal shell 4 and the metal shell 5 is produced at the same time by way of the spring clip 16, the connecting web 15 and the spring clip 17. It is ensured by this short-circuit of the capacitors 2 and 3 that the subject of the invention always comes into use free of potential or charge when this Is removed from the spring clip.

In use of the subject of the invention against an attack of pain, the tubular housing 1 is unclipped by the fingers in such a manner that the metal shell 5 (negative pole side) comes to lie against the hollow inner hand. The oppositely disposed end with the metal shell 4 (positive pole side) is pressed with light pressure against the place of pain in the body. A conductive connection is thereby produced between the nerve, which is conducting the pain signal, and the positive pole side of the capacitors 2 and 3 via the tissue and skin surface. The pulse-like voltage peaks, which occur on voltage inversion, in the nerve are thus reduced by the electric flux with the capacitors 2 and 3 or completely smoothed out. The nerve concerned thus signals freedom of pain to the brain.

Tests have shown that, for example in the case of strong back, muscle, joint and sciatica pains and in the case of painful calf cramps the intensity of pain was reduced abruptly or in switchlike manner to zero after about four (4) minutes through use of the subject of the invention. This means that the stronger the pain and thus analogously the voltage and pulse frequency in the nerve, the greater and more effective the compensation by the capacitors 2 and 3.

Figure 2:
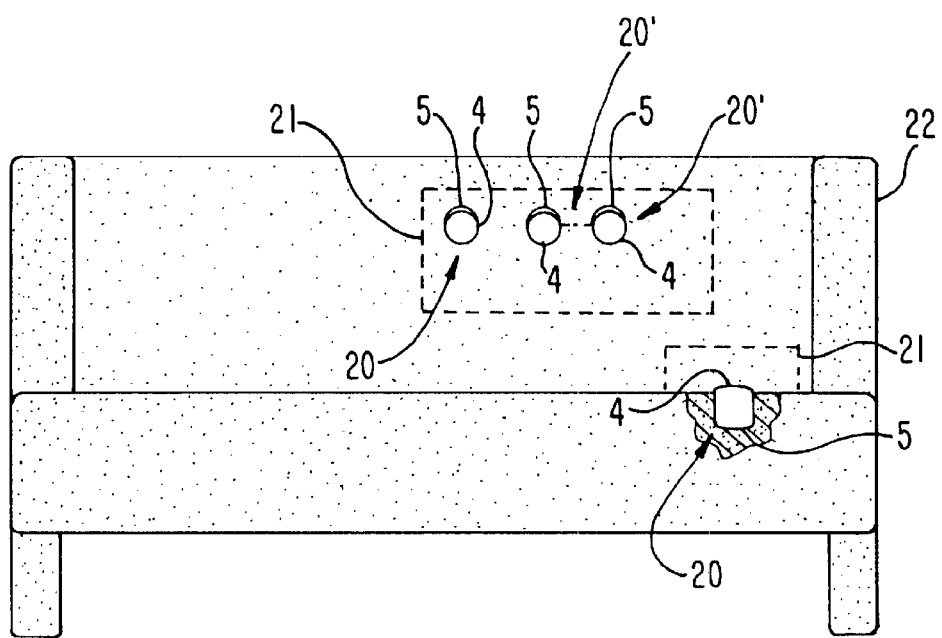

As shown in FIG. 2, in one embodiment a pole contact of an uncharged electrical capacitor 20 is made through contact with a skin surface 21 of a person, such that the uncharged electrical capacitor 20 in a fixed location in a piece of furniture 22, for sitting or lying, such as a chair, couch or bed, so that the positive pole 4 comes to constantly bear against the place of pain and a negative pole 5 is applied to a ground. In a further embodiment, a plurality of electrical capacitor 20' may be connected in parallel and fixed to the furniture 22.

Figure 3:
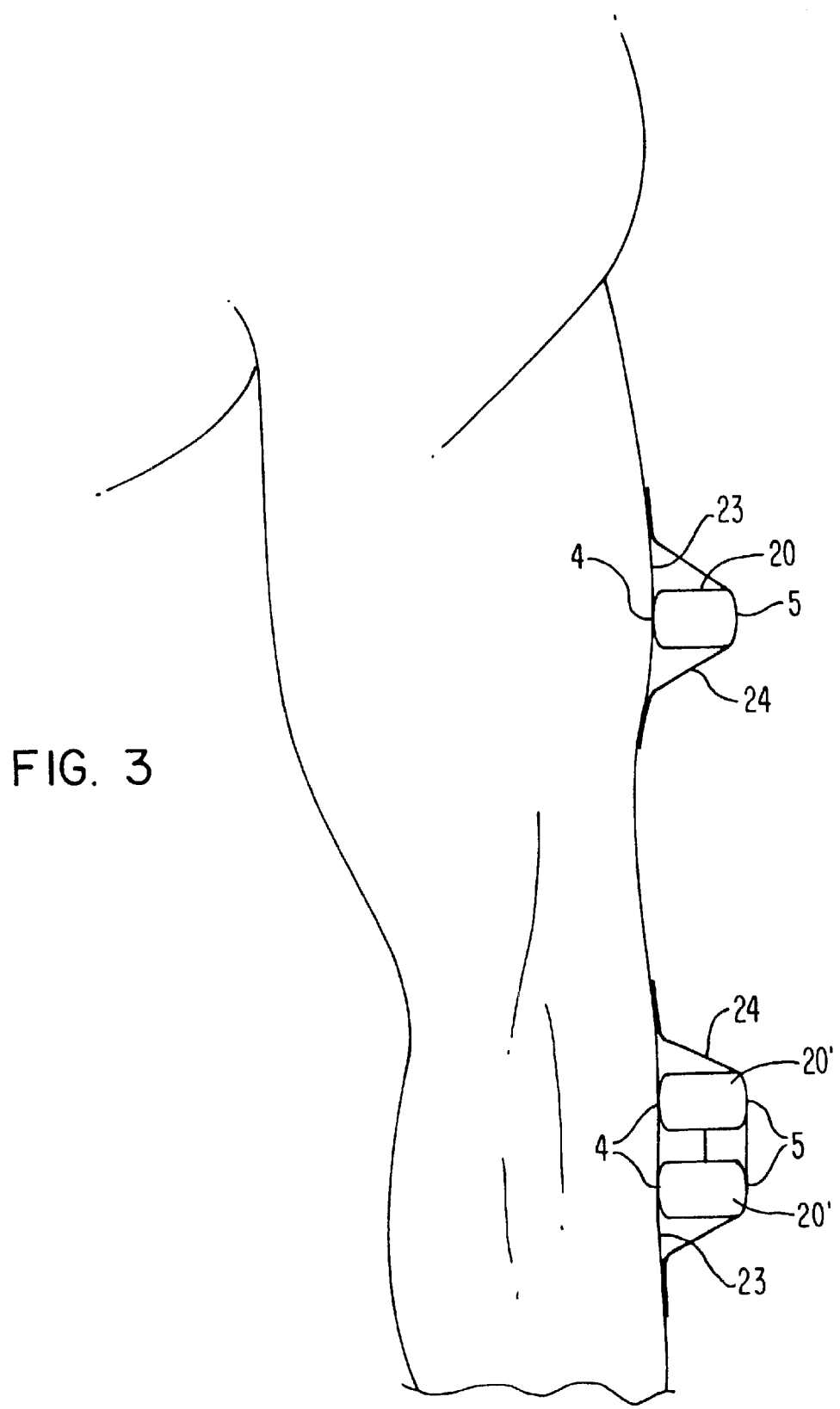

As shown in FIG. 3, pole contact of an uncharged electrical capacitor 20 is made through contact with a skin surface 23, wherein the capacitor 20 is fixed by means of a piece of material 24 against pain-conducting parts of a body of a patient so that the positive pole 4 of the capacitor 20 is directed to the place of pain and a negative pole 5 is drained off to remote parts of the body. In a further embodiment, a plurality of electrical capacitors 20' are connected in parallel.

Figure 4:
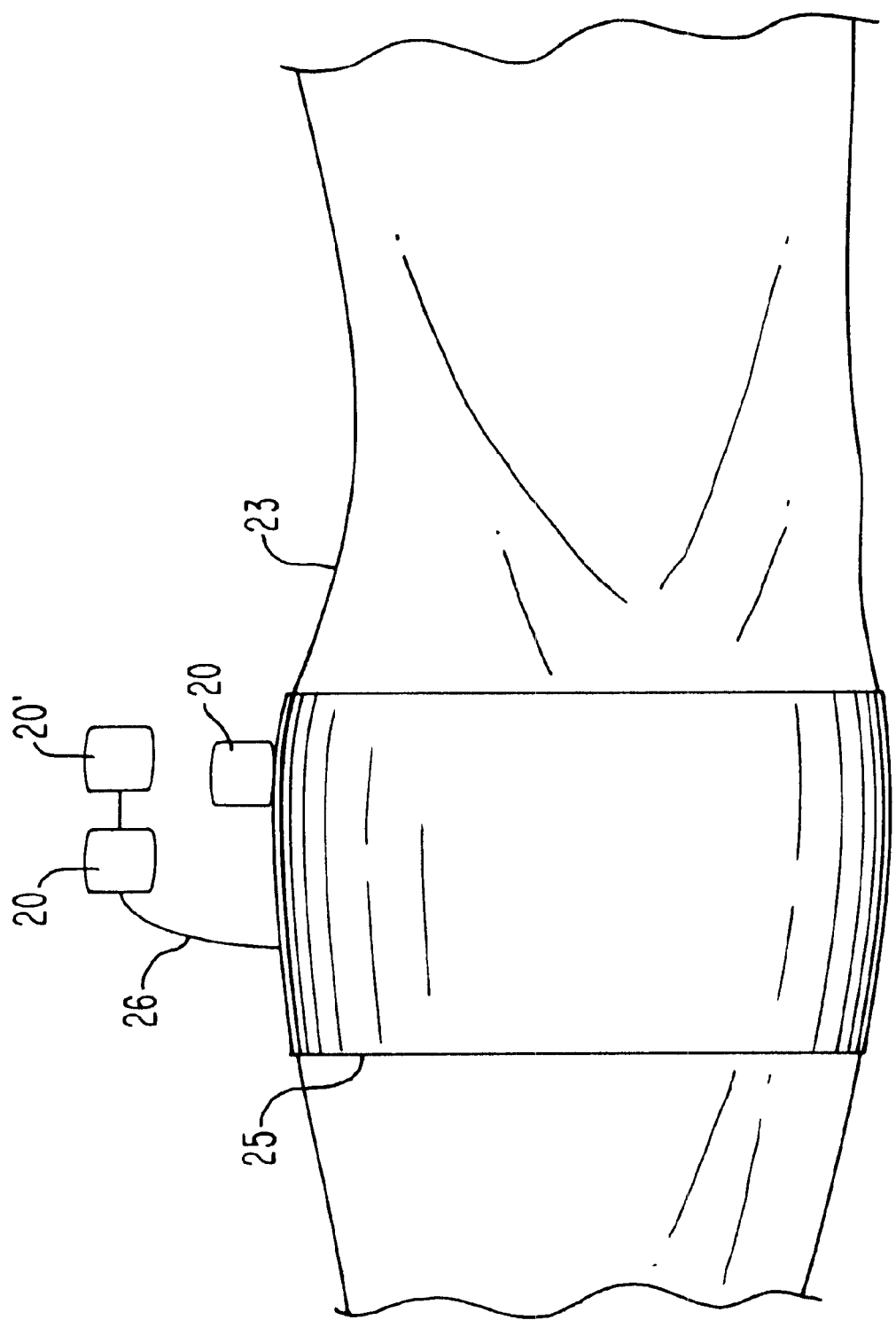

As shown in FIG. 4, in a further embodiment, pole contact of an uncharged electrical capacitor 20 is made through contact with a skin surface 23 by covering the surface of the skin 23 over the place of pain by means of a conductive metal foil 25, which contacts the skin surface 23. The foil is then connected with an uncharged electrical capacitor 20 directly or by use of a cable 26. Also a second uncharged electrical capacitor 20', connected in parallel, may be used.

As shown in FIG. 5, according to a further embodiment, pole contact of an uncharged electrical capacitor 20a, or a plurality of uncharged electrical capacitors 20a', is made by a conductive connection with a large-volume artery 26 of a patient directly. Alternatively, pole contact of an uncharged electrical capacitor 20b, or a plurality of uncharged electrical capacitors 20b', may be made through contact indirectly via the surface of the skin. Further, an electrical capacitor 20c may be used as an implant having a pole 4c contact the artery 26. A plurality of uncharged electrical capacitors 20c, may also be used as implants. capacitors 20c' may be connected in parallel and fixed to the furniture 22.

The use must be prolonged somewhat more, perhaps ten (10) minutes, if the nerve of a more deeply seated organ is to be treated, because possible air voids or bone parts attenuate the electric flux to the capacitors 2 and 3.

The time for the ensuing freedom of pain subjectively assessed by the patient after a treatment was reported at about two (2) hours to several days, wherein compensation for strong pains lasts rather longer in terms of time than for less-strong pains.

It is self-evident that voltage peaks in the thus-called motor nerves, for example in the case of a tremor attack, can also be reduced or smoothed out by the subject of the invention.

It has also been found that a short-circuit bridge between the positive and negative poles of the capacitors 2 and 3 increases the dynamic capacity of the capacitors 2 and 3. This has the advantage that the capacitors 2 and 3 in the static state are no longer permanently chargeable and thus undesired discharging currents and discharging voltages are at the same time made impossible.

The dynamic pulse-like electric flux around the static zero potential of the capacitors 2 and 3 relative to the nerve is thereby improved in the range of about 3 to 500 Hertz. The spring holder 15, 16, 17 for the discharging of the capacitors over time can be omitted.

If the place of pain or the pain-transmitting nerve cannot be clearly localised, it is then advantageous to cover the place of pain at the skin surface with a metal foil, for example an aluminium foil, to wrap extremities, for example an arm or a leg, with the metal foil, and to connect the foil directly or by means of cable with the short-circuited capacitors 2 and 3, this procedure is also indicated for headaches of unknown genesis.

A further very effective method of treatment of pain is also achieved by a direct or indirect contact of the subject of the invention with large volume arteries. If, for example, the contact pole of the subject of the invention is brought to bear against the skin surface directly at the carotid artery (Carotis), then a conductive connection between the short-circuited capacitors 2 and 3 in the subject of the invention and the conductive pulsating blood in the artery is thereby produced and thus at the same time an electric flux between nerves, which are excited in pain, everywhere in the body of the patient and the subject of the invention. Both carotid arteries can also be brought Into contacting connection at the same time with the subject of the Invention by an external bridge, for example by means of a metal foil or a conductive metal neck band.

This process is thus to be understood in the sense that the capacitive field of the capacitors 2 and 3 in the subject of the invention is also extended to the entire volume of blood of the patient. Thus, apart from blocking pain, the electric potential enhanced in the vegetative nervous system by the pick up of so-called "electro-smog" from the environment or by change in weather can be reduced and thus a better well-being is imparted to the patient.

It is obvious that the subject of the invention can also be implanted, for example in miniature mode of construction, as a permanent unit below the skin surface in direct or indirect contact with an artery.

It is possible that the person or animal is disposed in a water bed, which in turn is connected with short-circuited capacitors of increased capacity, for the purpose of pain therapy.

The subject of the invention has meanwhile been successfully proven many times, wherein the use success rate in the case of intact, undamaged nerves lies at almost 100%.

Reference Numeral List
1. tubular housing
2. electric capacitor
3. electric capacitor
4. metal shell
5. metal shell
6. contact plate
7. contact plate
8. conductor wire
9. conductor wire
10. conductor wire
11. conductor wire
12. compression spring
13. compression spring
14. spring holder
15. connecting web
16. spring clip
17. spring clip

What is claimed is:

1. A method of inhibiting pain pulses in the nerves of humans and animals, wherein the pain pulse in a nerve is made up of excitation states of nerve cells in the form of a pulse-like current with corresponding voltage peaks, the method comprising the steps of:

causing a pain pulse to be displaced in phase by displacing the pulse-like current together with voltage peaks of the pulse-like current in phase so that the pain pulse is one of reduced and eliminated by an effect of the phase displacement, and wherein said step of causing the pain pulse to be displaced in phase includes bringing a pole of uncharged electrical capacitance means into contact with a skin surface over a place of an excited nerve, and one of reducing and completely smoothing out the voltage peaks of the pain pulse through a capacitance current of the capacitance means.

2. A method according to claim 1, wherein the pole contact is produced by mounting an uncharged electrical capacitor in a fixed location in one of a piece of furniture and a bed of a patient so that a positive pole comes to constantly bear against the place of pain and a negative pole is applied to a ground.

3. A method according to claim 2, wherein a plurality of uncharged electrical capacitors are used which are connected parallel so that the respective positive poles come to constantly bear against the place of pain and the respective negative poles are applied to a ground.

4. A method according to claim 1, wherein the pole contact is produced by fixing an uncharged electrical capacitor by means of one of a bandage and cloth against pain-conducting parts of a body of a patient so that a positive pole of the capacitor is directed to the place of pain and respective negative poles are drained off to remote parts of the body.

5. A method according to claim 4, wherein a plurality of uncharged electrical capacitors are used which are connected in parallel so that the respective positive poles are directed to the place of pain and the respective negative poles are applied to a ground.

6. A method according to claim 1, wherein the pole contact is produced by covering a large area of a deep-seated place of pain in a patient at the surface of the skin over the place of pain by means of a conductive metal foil contacting the skin surface all around the place of pain; and connecting the foil by one of a direct connection or by way of cable with an uncharged electrical capacitor.

7. The method according to claim 6, wherein a plurality of uncharged electrical capacitors are used which are connected in parallel.

8. A method according to claim 1, wherein the pole contact is produced by bringing an uncharged electrical capacitor into a conductive connection with a large-volume artery by one of making a connection 1) directly and 2) indirectly via the surface of the skin.

9. The method according to claim 8, wherein a plurality of uncharged electrical capacitors are used which are connected in parallel.

10. A method of inhibiting pain pulses in the nerves of humans and animals, wherein the pain pulse in a nerve is made up of excitation states of nerve cells in the form of a pulse-like current with corresponding voltage peaks, the method comprising the steps of:

causing a pain pulse to be displaced in phase by displacing the pulse-like current together with voltage peaks of the pulse-like current in phase so that the pain pulse is one of reduced and eliminated by an effect of the phase displacement, wherein said step of causing the pain pulse to be displaced in phase includes bringing an uncharged electrical capacitor into a conductive connection with a large-volume artery of a patient as an implant, and one of reducing and completely smoothing out the voltage peaks of the pain pulse through a capacitance current of the capacitance means.

11. The method according to claim 10, wherein a plurality of uncharged electrical capacitors are used which are connected in parallel.

12. A method according to claim 1, wherein the pole contact is produced by disposing one of a person and animal in a water bed and connecting the bed with an uncharged electrical capacitor.

13. The method according to claim 12, wherein a plurality of uncharged electrical capacitors are used which are connected in parallel.

14. A method according to claim 1, wherein the capacitance of the capacitance least 10,000 microfarads.

15. A device for carrying out the method according to claim 10, comprising one of an electrical capacitor and a plurality of electrical capacitors connected in parallel and accommodated in a housing, a positive pole of the or each capacitor being connected with a large-area spherically rounded metal shell and a negative pole of the or each capacitor being similarly connected with an oppositely disposed, spherically rounded metal shell, the negative pole being contactable with one of a hand of a patient and therapist to lead a negative potential to ground.

16. A device according to claim 15, wherein the positive and negative poles of the capacitor or each of the capacitors are permanently connected together by means of a short-circuit bridge to form a resonant circuit.

\* \* \* \* \*